US00PP19923P2

(12) United States Plant Patent
Pieters

(10) Patent No.: US PP19,923 P2
(45) Date of Patent: Apr. 14, 2009

(54) *CHRYSANTHEMUM* PLANT NAMED 'PPP FORZ06'

(50) Latin Name: *Chrysanthemum morifolium*
Varietal Denomination: PPP FORZ06

(75) Inventor: Dirk Pieters, Oostnieuwkerke (BE)

(73) Assignee: Paraty BVBA, Oostnieuwkerke (BE)

( * ) Notice: Subject to any disclaimer, the term of this patent is extended or adjusted under 35 U.S.C. 154(b) by 40 days.

(21) Appl. No.: 11/823,269

(22) Filed: Jun. 27, 2007

(51) Int. Cl.
*A01H 5/00* (2006.01)

(52) U.S. Cl. ..... Plt./293; Plt./290

(58) Field of Classification Search ..... Plt./293, Plt./290
See application file for complete search history.

(56) References Cited

U.S. PATENT DOCUMENTS

PP18,094 P2 * 9/2007 Pieters ..... Plt./290

* cited by examiner

*Primary Examiner*—Wendy C. Haas

(57) ABSTRACT

A new and distinct *Chrysanthemum* plant cultivar is disclosed, characterized by large, decorative type inflorescences, consistent flowering response to short days, blooming consistently after 49 days of short day length, red-bronze ray florets, free branching habit, and a consistent natural season flowering habit during the third week of September.

1 Drawing Sheet

Latin name of the genus and species: *Chrysanthemum morifolium.*
Variety denomination: 'PPP FORZ06'.

BACKGROUND OF THE INVENTION

The new cultivar 'PPP FORZ06' is a product of a naturally occurring whole plant mutation of 'Forza Orange' (not patented in the United States). The new cultivar was discovered in an outdoor trial garden and selected as a single plant by Dirk Pieters in September of 2000 in a cultivated area of Oostnieuwkerke, Belgium.

Asexual reproduction of the new cultivar 'PPP FORZ06' by terminal cuttings was performed in Oostnieuwkerke, Belgium and Oxnard, Calif., and has shown that the unique features of this new cultivar are stable and reproduced true to type on successive generations.

SUMMARY OF THE INVENTION

The cultivar 'PPP FORZ06' has not been observed under all possible environmental conditions. The phenotype may vary somewhat with variations in environment such as temperature, daylength, and light intensity, without, however, any variance in genotype.

The following traits have been repeatedly observed and are determined to be the unique characteristics of 'PPP FORZ06.' These characteristics in combination distinguish 'PPP FORZ06' as a new and distinct *Chrysanthemum* cultivar:

1. Large, red-bronze, decorative type inflorescences;
2. Free branching habit;
3. Consistent natural season flowering habit during the third week of September; and
4. Consistent flowering response to short days, blooming consistently after 49 days of short day length.

Plants of the new cultivar 'PPP FORZ06' are similar to plants of the parent variety, 'Forza Orange' in most horticultural characteristics, however plants of the new cultivar 'PPP FORZ06' are shorter but have a wider plant spread. Also, the new cultivar 'PPP FORZ06' has a wider inflorescence diameter. Finally, 'PPP FORZ06' has red ray florets compared to the bright orange ray florets of the parent 'Forza Orange.'

In comparison to the commercially available variety 'PPP CON OR05' (U.S. Plant Pat. No. 18,094), 'PPP FORZ06' is smaller in both height and plant spread. Additionally, the new variety 'PPP FORZ06' has more leaves per lateral branch. Further, the new variety 'PPP FORZ06' has a smaller inflorescence diameter and has multicolored bronze-red ray florets compared to the orange-red ray florets of 'PPP CON OR05.'

BRIEF DESCRIPTION OF THE PHOTOGRAPH

The accompanying drawing illustrates in full color a typical plant of 'PPP FORZ06' grown in a 2 gallon container. One cutting was used in the pot, planted mid May and grown under outdoor field conditions. The colors are as nearly true as is reasonably possible in a color representation of this type.

DETAILED BOTANICAL DESCRIPTION

In the following description, color references are made to The Royal Horticultural Society Colour Chart except where general terms of ordinary dictionary significance are used. The following observations and measurements describe 'PPP FORZ06' plants grown in Oxnard, Ventura County, Calif., during the months of May through October 2006. The growing temperature ranged from 12° C. to 15° C. at night to 12° C. to 20° C. during the day. Measurements and numerical values represent averages of typical flowering types.

Botanical classification: *Chrysanthemum morifolium* cultivar 'PPP FORZ06.'
Commercial classification: Garden-type *Chrysanthemum.*

PROPAGATION

Time to rooting: 7 to 14 days at approximately 21° C.
Root description: Fine, fibrous.

PLANT

Growth habit: Mounding herbaceous perennial.
Height: Approximately 21 cm.
Plant spread: Approximately 42 cm.
Growth rate: Moderate.
Branching characteristics: Free Branching.
Length of lateral branches: Approximately 17 cm.
Number of leaves per lateral branch: Approximately 24.
Age of plant described: Approximately 148 days.

FOLIAGE

Leaf:
*Arrangement.*—Alternate single.
*Average length.*—Approximately 5.7 cm.
*Average width.*—Approximately 2.8 cm.
*Shape of blade.*—Ovate.
*Apex.*—Acuminate.
*Base.*—Attenuate.
*Attachment.*—Stalked.
*Margin.*—Serrate.
*Texture of top surface.*—Lightly pubescent.
*Texture of bottom surface.*—Lightly pubescent.
*Leaf internode length.*—Approximately 1 cm.
*Color.*—Young foliage upper side: Near Yellow-Green 147A. Young foliage under side: Near Yellow-Green 148A. Mature foliage upper side: Near Green 137A. Mature foliage under side: Near Yellow-Green 148A.
*Venation.*—Type: Palmately net. Venation color upper side: Near Yellow-Green 147B. Venation color under side.: Near Yellow-Green 148B.
Petiole:
*Average length.*—Approximately 1.2 cm.
*Color.*—Near Yellow-Green 148B.
*Diameter.*—Approximately 0.2 cm.

BLOOM

Inflorescence:
*Flowering habit.*—Induced by darkness period greater than 13.5 hours, approximately 49 days of appropriate day length required to induce and develop blooms.
*Inflorescence form.*—Decorative.
*Natural flowering season.*—Approximately the third week in September.
*Number of inflorescences per lateral branch.*—Approximately 7.
*Inflorescence diameter.*—Approximately 4.5 cm.
*Inflorescence depth.*—Approximately 1.3 cm.
*Inflorescence longevity on plant.*—Approximately 28 to 33 days.
*Persistence.*—Persistent.
Ray florets:
*Appearance.*—Matte.
*Texture.*—Smooth.
*Average number of ray florets per inflorescence.*—172.
*Shape.*—Oblanceolate.
*Aspect.*—Flat.
*Margin.*—Entire.
*Apex.*—Obtuse.
*Length.*—Approximately 1.6 cm.
*Width.*—Approximately 0.4 cm.
*Color.*—Upper surface at first opening: Base: Near Yellow 9A. Center: Near Greyed-Orange 172D. Apex: Near Red 46A. Upper surface at maturity: Base: Near Yellow 9A. Center: Near Greyed-Orange 171B. Apex: Near Red 46A. Upper surface at fading: Base: Near Yellow 9A. Center and apex: Near Greyed-Orange 172C. Under surface at first opening: Base: Near Yellow 9A. Center and apex: Near Greyed-Red 181B. Under surface at maturity: Base: Near Yellow 9A. Center and apex: Near Greyed-Red 181A. Under surface at fading: Base: Near Yellow 9A. Center and apex: Near Greyed-Red 181A.
Disc florets:
*Appearance.*—Shiny.
*Texture.*—Smooth.
*Average number of florets per disc.*—Approximately 20.
*Shape.*—Cylindric.
*Apex.*—Obtuse.
*Average length.*—Approximately 0.4 cm.
*Average width.*—Approximately 0.1 cm.
*Color.*—At first opening: Near Yellow 12A. At maturity: Near Yellow 13A. At fading: Near Yellow 13C.
Peduncle:
*Length.*—At terminal end (shortest): Approximately 2.5 cm. At lateral end (longest): Approximately 7 cm.
*Angle to stem.*—Acute.
*Strength.*—Moderate.
*Color.*—Near Green 137C.
*Habit.*—Upright.
*Diameter.*—Approximately 0.1 cm.
*Surface texture.*—Lightly pubescent.
Inflorescence bud:
*Length.*—Approximately 1 cm.
*Diameter.*—Approximately 1 cm.
*Form.*—Globular.
*Color.*—Near Greyed-Purple 183C.
Involucral bracts (phyllaries):
*Appearance.*—Matte.
*Texture.*—Lightly pubescent.
*Number.*—Approximately 28.
*Shape.*—Ovate.
*Margin.*—Entire.
*Apex.*—Acute.
*Length.*—Approximately 0.7 cm.
*Width.*—Approximately 0.3 cm.
*Color.*—Upper side: Near Green 137A. Under side: Near Green 137A.

REPRODUCTIVE ORGANS

Ray florets:
*Number of pistils per floret.*—1.
*Stigma shape.*—2 branched.
*Stigma color.*—Near Yellow 9A.
*Style color.*—Near Yellow-Green 154D.
*Style length.*—Approximately 0.4 cm.
*Stamens.*—Absent.
Disc florets:
*Number of pistils per floret.*—1.
*Stigma shape.*—Cylindric.
*Stigma color.*—Near Yellow 13A.
*Style length.*—Approximately 0.1 cm.

*Style color.*—Near Yellow-Green 154D.
*Number of stamens per floret.*—Approximately 5.
*Anther shape.*—Tubular.
*Anther color.*—Near Yellow 13B.
*Pollen color.*—No pollen detected.

OTHER CHARACTERISTICS

Disease resistance: Neither resistance nor susceptibility to diseases or pests has been observed in this variety.

Drought tolerance/cold tolerance: Flowering plants are hardy to low temperatures about −2° C. Non-flowering plants are hardy in the approximate range of 3° C. to −6° C., depending upon duration of cold and amount of moisture in the soil. With adequate water plants are hardy to a high temperature of 45° C.

Fruit/seed production: Commercially, this plant is not used or observed in a stage where seeds would be produced. Therefore, seed production has not been observed.

What is claimed is:

1. A new distinct cultivar of *Chrysanthemum* plant named 'PPP FORZ06' as herein illustrated and described.

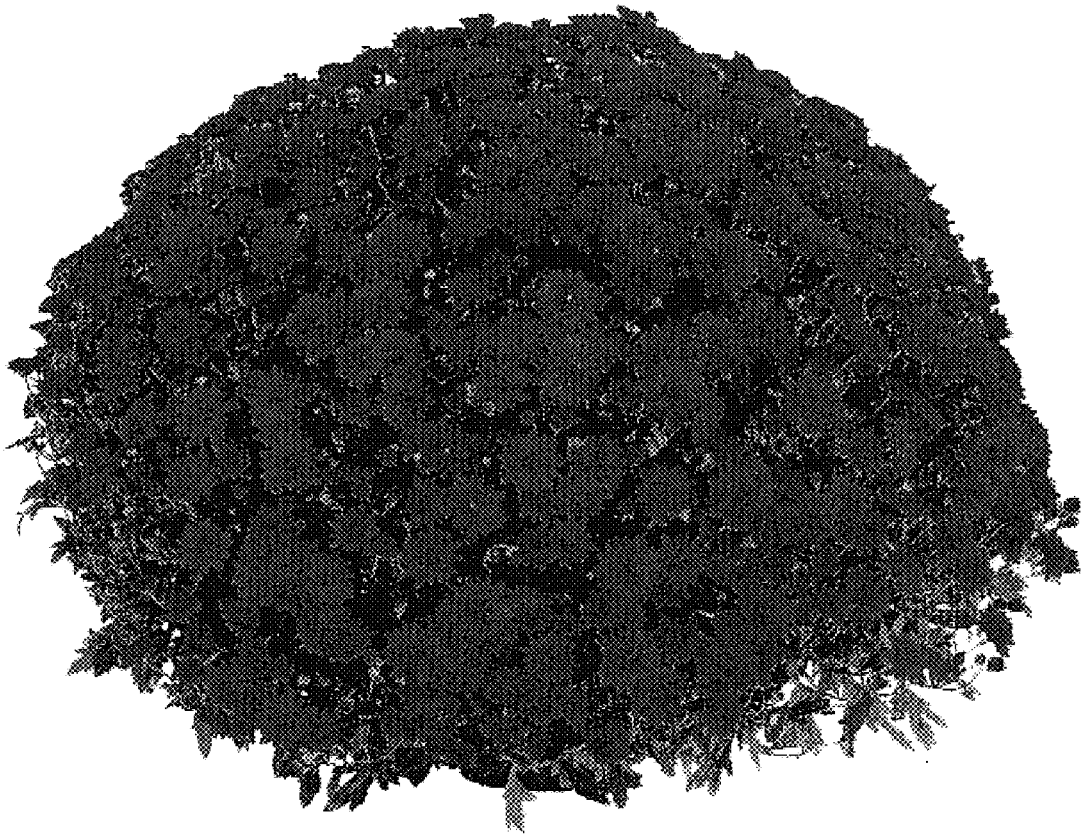

* * * * *